(12) United States Patent
Leying et al.

(10) Patent No.: US 9,702,017 B2
(45) Date of Patent: Jul. 11, 2017

(54) HEV ASSAY

(71) Applicant: Roche Molecular Systems, Inc., Pleasanton, CA (US)

(72) Inventors: Hermann Leying, Rotkreuz (CH); Thomas W. Myers, Sunnyvale, CA (US); Nicolas Newton, Oakland, CA (US); Eberhard Russmann, Huenenberg See (CH); Joseph San Filippo, Dublin, CA (US); Nancy Schoenbrunner, Moraga, CA (US); Heike Wilts, Cham (CH); Xiaoning Wu, Fremont, CA (US); Karen K. Y. Young, San Ramon, CA (US); Dirk Zimmermann, Zug (CH)

( * ) Notice: Subject to any disclaimer, the term of this patent is extended or adjusted under 35 U.S.C. 154(b) by 0 days.

(21) Appl. No.: 13/864,439

(22) Filed: Apr. 17, 2013

(65) Prior Publication Data
US 2013/0280697 A1 Oct. 24, 2013

Related U.S. Application Data

(60) Provisional application No. 61/625,816, filed on Apr. 18, 2012.

(51) Int. Cl.
*C12Q 1/68* (2006.01)
*C12Q 1/70* (2006.01)

(52) U.S. Cl.
CPC ......... *C12Q 1/707* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2003/0152925 A1 | 8/2003 | Chun | |
| 2004/0101820 A1* | 5/2004 | Takahashi et al. | 435/5 |
| 2010/0173283 A1* | 7/2010 | Takahashi et al. | 435/5 |

FOREIGN PATENT DOCUMENTS

| | | |
|---|---|---|
| EP | 1400588 A1 | 3/2004 |
| EP | 12167064 | 7/2012 |
| JP | 2007-222092 A | 9/2007 |
| WO | 9919732 A1 | 4/1999 |
| WO | 2006/009260 A1 | 1/2006 |
| WO | 2007/133682 A2 | 11/2007 |
| WO | 2010055184 A1 | 5/2010 |
| WO | PCT/EP2013/057783 | 8/2013 |

OTHER PUBLICATIONS

Jothikumar et al. (A broadly reactive one-step real-time RT-PCR assay for rapid and sensitive detection of hepatitis E virus, Journal of Virological Methods 131 (2006) 65-71).*
Tan et al. (DNA, RNA, and Protein Extraction: The Past and the Present, Journal of Biomedicine and Biotechnology, vol. 2009, Article ID 574398, 10 pages, Nov. 5, 2009).*
Huang et al. (Detection by Reverse Transcription PCR and Genetic Characterization of Field Isolates of Swine Hepatitis E Virus from Pigs in Different Geographic Regions of the United States, Journal of Clinical Microbiology, Apr. 2002, p. 1326-1332).*
Enouf et al. (Validation of Single Real-Time TaqMan PCR Assay for the Detection and Quantitation of Four Major Genotypes of Hepatitis E Virus in Clinical Specimens, Journal of Medical Virology 78:1076-1082 (2006)).*
Vasickova et al. (Optimisation of a triplex real time RT-PCR for detection of hepatitis E virus RNA and validation on biological samples, Journal of Virological Methods 180 (2012) 38-42, Dec. 22, 2011).*
Wenzel et al. (Detection of hepatitis E virus (HEV) from porcine livers in Southeastern Germany and high sequence homology to human HEV isolates, Journal of Clinical Virology 52 (2011) 50-54).*
Nolan et al. (Quantification of mRNA using real-time RT-PCR, Nat Protoc. 2006;1(3):1559-82).*
Boutros et al. (UniPrime2: a web service providing easier Universal Primer design, Nucleic Acids Res. Jul. 2009;37(Web Server issue): Epub Apr. 28, 2009).*
Kalendar et al. (Java web tools for PCR, in silico PCR, and oligonucleotide assembly and analysis, Genomics. Aug. 2011;98(2):137-44. Epub May 3, 2011).*
Singh et al. (PCR Primer Design, Molecular Biology Today 2001. 2(2): 27-32).*
Apte et al. (AlleleID: a pathogen detection and identification system, Methods Mol Biol. 2007;402:329-46, Dec. 31, 2007).*
Fredslund et al. (Primique: automatic design of specific PCR primers for each sequence in a family, BMC Bioinformatics, Dec. 2007, 8:369, Oct. 3, 2007).*
Hakze-Van Der Honing, Renate W., et al., 2011, "First Isolation of Hepatitis E Virus Genotype 4 in Europe through Swine Surveillance in the Netherlands and Belgium", Plos One, 6(8):e22673.
Troxler, Salome, et al., 2011, "TaqMan Real-Time Reverse Transcription-PCR Assay for Universal Detection and Quantification of Avian Hepatitis E Virus from Clinical Samples in the Presence of a Heterologous Internal Control RNA", Journal of Clinical Microbiology, 49(4):1339-1346.
Wenzel, Jurgen J., et al., 2011, "Detection of hepatitis E Virus (HEV) from porcine livers in Southeastern Germany and high sequence homology to human HEV isolates", Journal of Clinical Virology, 52:50-54.
Gahoi et al. DPPrimer—A Degenerate PCR Primer Design Tool, Bioinformation 9(18): 937-940 (2013).
Gardner, et al., "Limitations of TaqMan PCR for Detecting Divergent Viral Pathogens Illustrated by Hepatitis A, B, C, and E Viruses and Human Immunodeficiency Virus," Journal of Clinical Microbiology 41(6):2417-2427 (2003).
Murphy and Bustin, "Reliability of real-time reverse-transcription PCR in clinical diagnostics: gold standard or substandard?," Expert Rev. Mol. Diagn. 9(2):187-197 (2009).
Peters, et al., "Real-time RT-PCR: considerations for efficient and sensitive assay design," Journal of Immunological Methods 286:203-217 (2004).

(Continued)

*Primary Examiner* — Aaron Priest
(74) *Attorney, Agent, or Firm* — Eric Grant Lee; Jeff Bernhardt

(57) ABSTRACT

A method of simultaneously amplifying genotypes 1, 2, 3 and/or 4 of HEV is disclosed comprising amplifying the genotypes 1, 2, 3 and/or 4 of HEV with one single nonedegenerate forward primer partially overlapping the 5'UTR region of HEV and at least one reverse primer. Also disclosed are related methods comprising a probe, and kits for the detection of genotypes 1, 2, 3 and/or 4 of HEV.

20 Claims, 1 Drawing Sheet

(56) References Cited

OTHER PUBLICATIONS

Smith and Osborn, "Advantages and limitations of quantitative PCR (Q-PCR)-based approaches in microbial ecology," FEMS Microbiol Ecol 67:6-20 (2009).

Ayyadevara, et al., Discrimination of Primer 3'-Nucleotide Mismatch by Taq DNA Polymerase during Polymerase Chain Reaction, Analytical Biochemistry 284:11-18 (2000).

Methods in Molecular Biology, Springer Protocols: RT-PCR Protocols, Second Edition, Edited by Nicola King, Human Press (2010).

Baylis, Sally A., et al., 2011, "Standardization of Hepatitis E Virus (HEV) Nucleic Acid Amplification Technique-Based Assays: an Initial Study to Evaluate a Panel of HEV Strains and Investigate Laboratory Performance", Journal of Clinical Microbiology, 49(4):1234-1239.

Enouf, V., et al., 2006, "Validation of Single Real-Time TaqMan(R) PCR Assay for the Detection and Quantitation of Four Major Genotypes of Hepatitis E Virus in Clinical Specimens", Journal of Medical Virology, 78:1076-1082.

Gyarmati, Peter, et al., 2007, "Universal detection of hepatitis E virus by two real-time PCR assays: TaqMan(R) and Primer-Probe Energy Transfer", Journal of Virological Methods, 146:226-235.

Jothikumar, Narayanan, et al., 2005, "A broadly reactive one-step real-time RT-PCR assay for rapid and sensitive detection of hepatitis E virus", Journal of Virological Methods, 131:65-71.

Vasickova, P., et al., 2007, "Hepatitis E virus: a review", Veterinarni Medicina, 52(9):365-384.

* cited by examiner

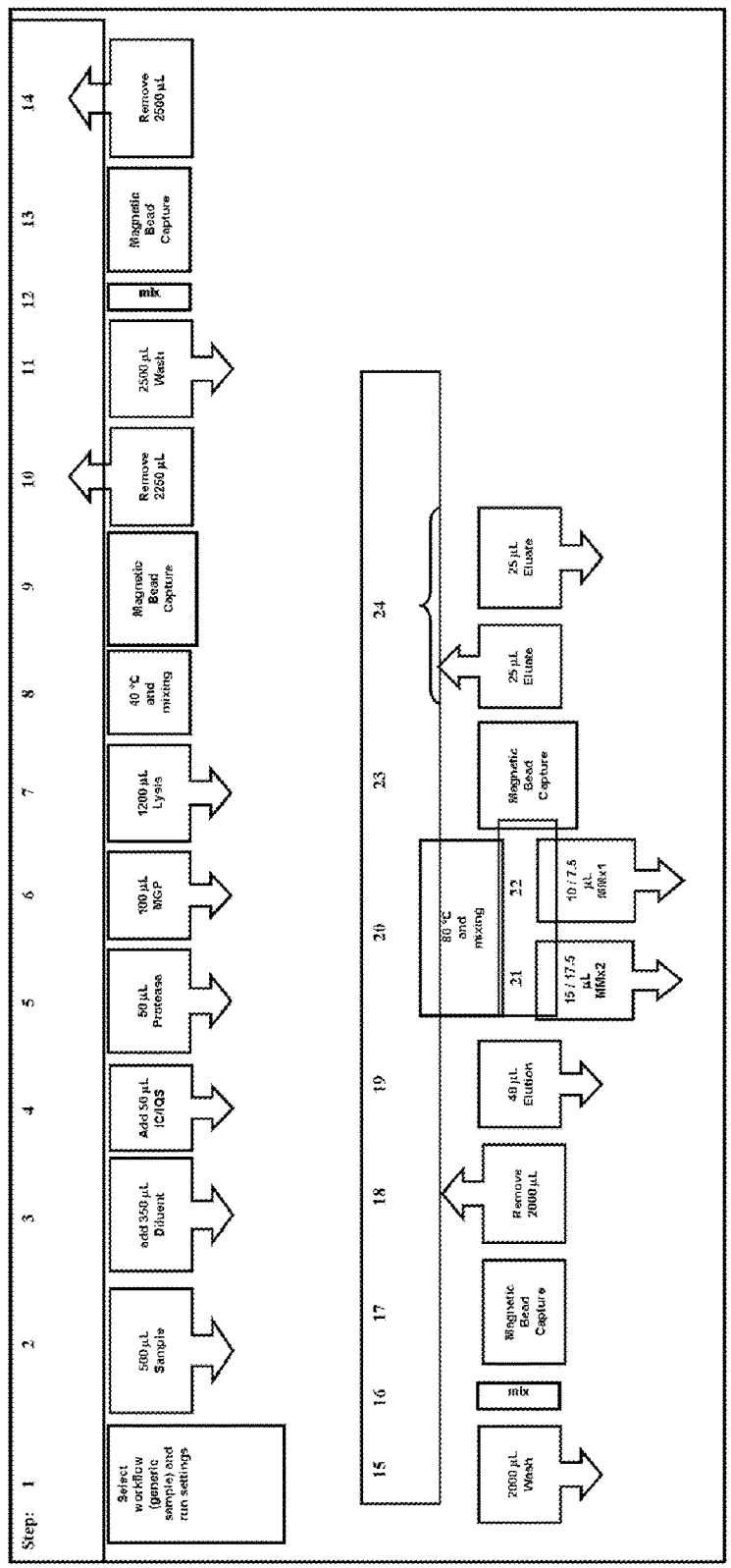

HEV ASSAY

CROSS-REFERENCE TO RELATED APPLICATIONS

The present application claims the benefit of U.S. Provisional Application No. 61/625,816 filed on Apr. 18, 2012. The entire disclosure of the above-referenced application is hereby incorporated herein by reference.

SEQUENCE LISTING

The instant application contains a Sequence Listing which has been submitted in ASCII format via EFS-Web and is hereby incorporated by reference in its entirety. Said ASCII copy, created on May 21, 2013, is named 30851-US1_SL.txt and is 15,028 bytes in size.

FIELD OF THE INVENTION

The invention relates to diagnostic tests, primer sets, oligonucleotide sets and kits for detecting HEV infection.

HEV infection results in hepatitis E, an acute disease. HEV is a non-enveloped, single stranded, positive sense RNA virus that is classified in the family Hepeviridae. There are four main genotypes of HEV causing infections in humans, genotypes 1, 2, 3 and 4. Diagnostic testing for HEV is important for people for which other causes of acute hepatitis have been excluded.

Different regions of HEV have been used for the design of nucleic acid based testing for HEV. ORF2 and ORF3 of HEV have been mostly used for detecting HEV by nucleic acid amplification. JP04080995 and JP04127722 have proposed the use of degenerate primers with multiple degenerate positions for a nested primer amplification approach based on primers which are partly located in the 5'UTR region of HEV.

BRIEF SUMMARY OF THE INVENTION

The invention relates to a method for simultaneously amplifying genotypes 1, 2, 3 and/or 4 of HEV if present in a biological sample, comprising the steps of
  (a) isolating nucleic acids present in the biological sample;
  (b) amplifying the nucleic acids isolated in step (a) using one non-degenerate forward primer and at least one non-degenerate reverse primer, wherein the forward and reverse primers are capable of simultaneously amplifying genotypes 1, 2, 3, and 4 of HEV.

In another aspect, the forward primer comprises a sequence selected from SEQ ID NOS: 1 to 6 and the one or more reverse primers comprise a sequence selected from SEQ ID NOS: 7 to 14. In another aspect, the forward primer comprises SEQ ID NO:6 and the one or more reverse primers comprise a sequence selected from SEQ ID NOS: 7 to 14.

In one aspect, the invention relates to a set of primers comprising a forward primer and at least one reverse primer, wherein the nucleic acid sequence of the forward primer comprises SEQ ID NO: 6, and wherein the nucleic acid sequence of the at least one reverse primer, or the reverse primer is selected from the group consisting of SEQ ID NOS: 7-14.

In one aspect the invention relates to a set of oligonucleotides, wherein the set consists of a set of primers as described herein, and one probe, wherein the probe comprises at least 20 contiguous nucleotides or at least 22 to 35 contiguous nucleotides of SEQ ID NO: 15-19 or 25, or a complementary sequence thereof.

In one aspect, the invention relates to the use of a set of primers or oligonucleotides as described herein for simultaneously detecting genotypes 1, 2, 3 and/or 4 of HEV in a biological sample.

In one aspect, the invention relates to a kit comprising a template dependent DNA polymerase, nucleotides and a set of primers or oligonucleotides as described herein.

SHORT DESCRIPTION OF FIGURES

FIG. 1 shows the workflow for isolation of the nucleic acids from a liquid sample.

DETAILED DESCRIPTION

The invention relates to a method for simultaneously amplifying genotypes 1, 2, 3 and/or 4 of HEV if present in a biological sample, comprising the steps of
  (a) isolating nucleic acids present in the biological sample;
  (b) amplifying the nucleic acids isolated in step (a) using one non-degenerate forward primer and at least one non-degenerate reverse primer, wherein the forward and reverse primers are capable of simultaneously amplifying genotypes 1, 2, 3, and 4 of HEV, In another aspect, the forward primer comprises a sequence selected from SEQ ID NOS: 1 to 6 and the one or more reverse primers comprise a sequence selected from SEQ ID NOS: 7 to 14. In another aspect, the forward primer comprises SEQ ID NO: 6 and the one or more reverse primers comprise a sequence selected from SEQ ID NOS: 7 to 14.

In one specific embodiment, the nucleic acid sequence of the forward primer comprises SEQ ID NO: 6 and the nucleic acid sequence or sequences of the at least one reverse primers are selected from the group consisting of SEQ ID NOS: 7 to 14. In another specific embodiment, the nucleic acid sequence of the forward primer comprises SEQ ID NO: 6, and the nucleic acid sequences of a mixture of two reverse primers comprise SEQ ID NO: 13 and SEQ ID NO: 14. In another specific embodiment, the nucleic acid sequence of the forward primer consists of SEQ ID NO: 6 and the nucleic acid sequence of the reverse primer comprises SEQ ID NO: 7. In another specific embodiment, the nucleic acid sequence of the forward primer consists of SEQ ID NO: 6 and the nucleic acid sequence of the reverse primer comprises SEQ ID NO: 13. In another specific embodiment, the nucleic acid sequence of the forward primer consists of SEQ ID NO: 6 and the nucleic acid sequence of the reverse primer comprises SEQ ID NO: 11.

The method has the advantage that genotypes 1, 2, 3 and/or 4 of HEV, or a combination thereof, can be simultaneously and efficiently amplified in a single reaction.

In one specific embodiment, the nucleic acids are isolated by binding to a solid phase.

In one specific embodiment, the method for amplifying HEV additionally comprises contacting the amplified nucleic acids with a probe under conditions sufficient for binding the probe to the amplified nucleic acids. In one specific embodiment thereof, the probe comprises at least 20, or 22 to 35 contiguous nucleotides of the nucleic acid sequence SEQ ID NOS: 15-19 or 25 or a complementary sequence thereof. In one specific embodiment, the nucleic acid sequence of the probe consists of a sequence selected from SEQ ID NOS: 15-19 or 25 or a complementary sequence thereof. In one specific embodiment thereof, the nucleic acid sequence of the probe consists of a sequence selected from SEQ ID NOS: 15-18 or 25 or a complementary sequence thereof. In one specific embodiment, the probe comprises a fluorophore and a quencher. Further, the fluorophore may be coupled to the 5' end of the probe, and wherein the spacing between fluorophore and quencher comprises at least 9 nucleotides.

Further specific embodiments of the method are described below.

The invention also relates to a method of simultaneously detecting genotypes 1, 2, 3 and/or 4 of HEV if present in a biological sample, comprising the steps of
  (a) isolating nucleic acids present in the sample
  (b) amplifying the nucleic acids isolated in step (a) using one non-degenerate forward primer and at least one non-degenerate reverse primer, wherein the forward and reverse primers are capable of amplifying genotypes 1, 2, 3, and 4 of HEV, and
  (c) detecting the amplified nucleic acid obtained in step (b) as an indication of the presence of at least one of genotypes 1, 2, 3 and/or 4 of HEV in the biological sample.

In another aspect, the forward primer comprises a sequence selected from SEQ ID NOS: 1 to 6 and the one or more reverse primers comprise a sequence selected from SEQ ID NOS: 7 to 14. In another aspect, the forward primer comprises SEQ ID NO: 6 and the one or more reverse primers comprise a sequence selected from SEQ ID NOS: 7 to 14.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The term "detecting" as used herein relates to the detection of a signal that correlates with the presence of the amplified nucleic acid. Detection may be quantitative or qualitative. The detection of the amplified nucleic acid provides an indication of the presence, or absence, of at least one of genotypes 1, 2, 3 and/or 4 of HEV in the biological sample.

The term "simultaneous detection" as used herein relates to the design of the method to detect different genotypes of HEV in a single reaction mixture. This necessitates that the primer and probe sequences used in the method are capable of generating a reasonable detection signal for all of the genotypes to be detected simultaneously if present in the sample. If only one genotype is present in a sample, the method will detect only the one genotype, even if it is capable of detecting more than one of GT1, GT2, GT3 and/or GT4 in a single reaction.

The simultaneous detection of several genotypes (hereinafter abbreviated as GT) often requires the use of degenerate primers and probes to ensure that all of the required genotypes are detected, unless highly conserved regions are available which are suitable for designing non-degenerate primers and probes for amplification that allow detection of all genotypes. Such regions cannot always be identified. The prior art identified regions other than 5'UTR such as the Capsid region as suitable for designing assays to detect HEV. Prior art references proposes the use of degenerate primers, some of which comprise more than 3 degenerate positions and are, thus, highly degenerate, from the 5'UTR region for a nested primer approach. The requirement for highly degenerate primers and the necessity to perform a nested PCR suggest that the method disclosed in the prior art based on 5'UTR detection is not as sensitive as methods using primer sequences from conserved regions of ORF2 or ORF3. The term "5'UTR" is used herein for target sequences, primers and amplicons which at least partially overlap with the 5'UTR sequence of HEV.

The term "biological sample" relates to material that can be subjected to a diagnostic assay targeting nucleic acids and is usually derived from a biological source. In some embodiments, the biological sample is derived from a human and is a body liquid. In one embodiment of the invention, the biological sample is human blood, plasma, serum, urine, sputum, sweat, swab, pipettable stool, or spinal fluid. The biological sample may also be a tissue from which target nucleic acids may be extracted.

The term "non-degenerate" as used herein relates to a primer or probe nucleic acid in which every position is defined by a single nucleotide, i.e. is either an A, G, T or C, or for example U. The non-degenerate primer or probe is chemically synthesized with methods well known in the art and may be purified. The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "degenerate" as used herein relates to a primer or probe nucleic acid in which certain positions are not defined by a single, specific nucleotide. Thus, in such a degenerate position, the primer or probe sequence can be either one of at least two different nucleotides. Such positions often represent difference in genotypes of the target nucleic acid. A degenerate sequence may also be represented as a mixture of multiple non-degenerate individual sequences which, for the purpose of this invention, differ in at least two positions.

The use of non-degenerate primers and probes has several advantages. One advantage is that by detecting four genotypes using non-degenerate primers, the risk of mis-priming, of competition between different sequences in a degenerate primer composition and the sensitivity of the amplification are improved. It is, therefore, desirable to use at least a single non-degenerate forward or reverse primer for detecting multiple genotypes. The complementary primer—the reverse primer, where the forward primer is non-degenerate, or the forward primer, where the reverse primer is non-degenerate—may comprise at least one non-degenerate primer.

The terms "primer" and "probe" as used herein relate to an oligonucleotide sequence. In the context of this invention, the term "oligonucleotide" refers to components formed from a plurality of nucleotides as their monomeric units. The term "oligonucleotide" also includes modified oligonucleotides, i.e. the primer and/or the probe comprise a modified nucleotide or a non-nucleotide compound. The term "primers" further relates to such oligonucleotides which are used in amplification reactions and anneal to a target sequence. The term "probe" further relates to an oligonucleotide sequence which is hybridized to a target nucleic acid or an amplicon for the purpose of either qualitative or quantitative detection.

In the case of a probe, modifications may include dyes, such as FAM, HEX, JA270, CY5, CY5.5, Coumarin etc. and/or quencher molecules. Dye molecules may be coupled to linkers. Such dyes may, however, also be present in primers. Other exemplary modifications include a phosphate group at the 3' end. Such dye molecules and/or quencher molecules may be used for the detection of the targeted nucleic acid.

Common modifications of primers include modification of the 3' nucleotides to prevent unspecific amplification products such as primer dimers. Such modifications are well known in the art and include, as non-limiting examples, t-Butyl benzyl-dA or -Butyl benzyl-dC. Such modifications are also included in the term "primer".

The term "forward primer" as used herein, thus, is understood to mean one primer priming the sense strand of a nucleic acid to allow a polymerase to extend in one direction along one strand of the target nucleic acid, and the term "reverse primer" is understood to mean a primer priming the antisense strand of a nucleic acid to allow the polymerase to extend in one direction along the complementary strand of the target nucleic acid, such that a double stranded amplicon is obtained with, at one end, the forward primer sequence and the complementary thereof and, at the opposite end, the reverse primer sequence and the complementary thereof. In reactions in which a reverse transcription (RT) step is initially performed, the reverse primer also serves as the RT primer for reverse transcription. RT-PCR is a technology well known in the art. In one embodiment, an RT step is performed.

In one specific embodiment, one non-degenerate forward primer and at least one non-degenerate reverse primer are used. Alternatively, one non-degenerate reverse primer and at least one non-degenerate forward primer are used. In a further specific embodiment, one non-degenerate forward primer and a mixture of two non-degenerate reverse primers are used. Alternatively, a mixture of two non-degenerate forward primers and one non-degenerate reverse primer are used. In a specific embodiment, the two non-degenerate primers only differ in a single nucleotide position. This has the advantage that differences in nucleotide sequence of different genotypes can be compensated for and the genotypes can be detected in a single reaction while avoiding the disadvantages of using primers with more than one position of degeneracy.

It is, thus, understood that if one forward and at least one reverse primer are used, then a single forward primer sequence is used, while one or more reverse primer sequences can be used. If two reverse primers are used, then a mixture of two reverse primer sequences is used. Alternatively, if one reverse primer and at least one forward primers are used, then a single reverse primer sequence is used, while one or more forward primer sequences can be used. If two reverse primers are used, then a mixture of two reverse primer sequences is used.

The term "amplifying" relates to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification. One embodiment of PCR is real-time PCR, which is well known in the art and which combines amplification and detection.

In one aspect of the method, the nucleic acid sequence of the forward primer is selected from the group consisting of SEQ ID NOS: 1-6 and the nucleic acid sequence of the at least one reverse primer is selected from the group consisting of SEQ ID NOS: 7-14. Hit rates obtained with different combinations of these forward and reverse primers are shown in Table 3. Table 5 and Table 8 show that primer and probe sequences as described herein detect HEV genotypes GT1, GT2, GT3 and GT4. In one specific embodiment, the nucleic acid sequence of the forward primer is SEQ ID NOS: 1, 2, 3, 4 or 6. In a more specific embodiment, the nucleic acid sequence of the forward primer is SEQ ID NOS: 2, 3, 4 or 6. In a more specific embodiment, the nucleic acid sequence of the forward primer is SEQ ID NOS: 3, 4 or 6. In a specific embodiment, the nucleic acid sequence of the forward primer is SEQ ID NO: 6.

In a specific embodiment, the nucleic acid sequence of the reverse primer consists of SEQ ID NOS: 7, 8, 9, 10, 11, 13 or 14. In a more specific embodiment, the nucleic acid sequence of the reverse primer is SEQ ID NOS: 8, 9, 10, 11, 13 or 14. In a more specific embodiment, the nucleic acid sequence of the reverse primer is SEQ ID NOS: 9, 10, 11, 13 or 14. In a specific embodiment, the nucleic acid sequence of the two reverse primers consist of SEQ ID NO: 13 and SEQ ID NO: 14 and the nucleic acid sequence of the forward primer consists of SEQ ID NO: 6. In another specific embodiment, the nucleic acid sequence of the forward primer consists of SEQ ID NO: 6 and the nucleic acid sequence of the reverse primer consists of SEQ ID NO: 11. In another specific embodiment, the nucleic acid sequence of the forward primer consists of SEQ ID NO: 6 and the nucleic acid sequence of the reverse primer consists of SEQ ID NO: 13. In another specific embodiment, the nucleic acid sequence of the forward primer consists of SEQ ID NO: 6 and the nucleic acid sequence of the reverse primer consists of SEQ ID NO: 7.

In one aspect, at least two of GT1, GT2, GT3 and/or GT4 may be detected simultaneously if present in a single reaction. In one specific embodiment, at least GT1, GT2, GT3 and GT4 may be detected simultaneously if present in a single reaction. In a further specific embodiment, GT1, GT2, GT3 and GT4 may be detected simultaneously if present in a single reaction.

In one aspect, the method additionally comprises isolating the nucleic acids, wherein the isolating of the nucleic acids precedes step (b), and wherein the isolated nucleic acids are amplified in step (b).

The term "isolating nucleic acids" relates to the release of nucleic acids from cells or viral particles known as lysis, followed by enrichment of the nucleic acids. Such isolation increases the availability of the target nucleic acid to primers for amplification, and also removes potential inhibitors of the subsequent amplification reaction that may be present in the sample. In one specific embodiment, the nucleic acids are isolated by binding to a solid phase. One useful procedure for binding nucleic acids entails the selective binding of nucleic acids to glass surfaces of binding particles such as e.g. magnetic particles in chaotropic salt solutions and separating the nucleic acids from contaminants such as agarose, proteins or cell debris. In some embodiments, the glass of the particles is formed using the gel sol process described in WO 96/41811 and then dried and compressed.

In one specific embodiment, the method additionally comprises, between steps (b) and (c), (b1) contacting the amplified nucleic acids with a probe under conditions sufficient for binding the probe to the amplified nucleic acids, and wherein the detecting in step (c) comprises
detecting the binding product between the amplified target nucleic acid and the probe as an indication of the presence of at least one of genotypes 1, 2, 3 and/or 4 of HEV in the biological sample. Detecting the amplified nucleic acid from step (b) may also be done without the use of a probe by standard detection methods well known in the art for example gel electrophoresis or other techniques for detection.

In a specific embodiment, the probe has a non-degenerate nucleic acid sequence. This has, again, the advantage that mis-priming during hybridization or interference between probe molecules of a degenerate probe is avoided and the sensitivity of detection is improved. The probe has to be able to hybridize to a sequence of the amplicon generated by amplification using forward and reverse primer(s). In a specific embodiment, the probe may hybridize to a sequence of the amplicon that does not overlap with the primer sequences. The amplicon is understood to relate to the product of at least one step of amplification using the forward and reverse primer(s).

In one aspect, the probe comprises at least 20, or 22 to 35 contiguous nucleotides of the nucleic acid sequence SEQ ID NOS: 15-19 or 25 or a complementary sequence thereof.

In one specific aspect the probe has a nucleic acid sequence selected from SEQ ID NOS: 15-19 or 25 or a complementary sequence thereof. The performance of these probes in detection of HEV genotypes is shown in Table 4. In one specific embodiment, the probe has a nucleic acid sequence selected from SEQ ID NOS: 15-18. In a further specific embodiment, the probe has a nucleic acid sequence selected from SEQ ID NOS: 15 and 18.

Specific embodiments of the methods, set of primers, set of oligonucleotides and kit herein described comprise the following combinations of primer nucleic acid sequences: SEQ ID NO: 1 combined with SEQ ID NOS: 8, 10, 11, 13 or 13 mixed with 14; SEQ ID NO: 2 combined with SEQ ID NOS: 8, 9, 10, 11, 13 or 13 mixed with 14; SEQ ID NO: 3 combined with SEQ ID NOS: 7, 8, 9, 10, 11, 12, 13 or 13 mixed with 14; SEQ ID NO: 4 combined with SEQ ID NOS: 7, 8, 9, 10, 11, 12, 13 or 13 mixed with 14; SEQ ID NO: 5 combined with SEQ ID NOS: 10, 11 or 13 or 13 mixed with 14; SEQ ID NO: 6 combined with SEQ ID NOS: 7, 8, 9, 10, 11, 12, 13 or 13 mixed with 14. SEQ ID NO: 7 combined with SEQ ID NOS: 3 or 4 or 6; SEQ ID NO: 8 combined with SEQ ID NOS: 2, 3 or 4 or 6; SEQ ID NO: 9 combined with SEQ ID NOS: 2, 3, 4, 5 or 6; SEQ ID NO: 10 combined with SEQ ID NOS: 1, 2, 3, 4, 5 or 6; SEQ ID NO: 11 combined with SEQ ID NOS: 1, 2, 3, 4, 5 or 6; SEQ ID NO: 12 combined with SEQ ID NOS: 3 or 4. Further specific embodiments of nucleic acid sequences of forward and reverse primer combinations are SEQ ID NO: 6 combined with SEQ ID NO: 7, SEQ ID NO: 6 combined with SEQ ID NO: 13, SEQ ID NO: 6 combined with SEQ ID NO: 13 and SEQ ID NO: 14, and SEQ ID NO: 6 combined with SEQ ID NO: 11. In one specific embodiment the nucleic acid sequence of the forward primer consists of SEQ ID NO: 6. In one specific embodiment, the forward primer whose nucleic acid sequence consists of SEQ ID NO: 6 is combined with a reverse primer, wherein the nucleic acid sequence of the reverse primer consists of SEQ ID NO: 7. In another specific embodiment, the forward primer whose nucleic acid sequence consists of SEQ ID NO: 6 is combined with a reverse primer, wherein the nucleic acid sequence of the reverse primer consists of SEQ ID NO: 13. In another specific embodiment, the forward primer whose nucleic acid sequence consists of SEQ ID NO: 6 is combined with a reverse primer, wherein the nucleic acid sequence of the reverse primer consists of SEQ ID NO: 11. In another specific embodiment, the forward primer whose nucleic acid sequence consists of SEQ ID NO: 6 is combined with a mixture of two reverse primers, wherein the nucleic acid sequences of the reverse primers consists of SEQ ID NO: 13 and SEQ ID NO: 14.

The advantage of these sets of primers, the methods in which these sets of primers are used and the kit comprising these sets of primers is that all four genotypes, 1, 2, 3, and 4 of HEV can be efficiently amplified and detected in a single reaction without cross-reactivity with unrelated microorganisms. A further advantage is that the test is simplified since all oligonucleotides can be synthesized with a specific, non-degenerate sequence. This significantly improves the quality of the oligonucleotides and the sensitivity and specificity of the method. Furthermore, since, besides the internal control oligonucleotides, only three to four HEV specific oligonucleotides (including the probes) are used for simultaneously detecting all four genotypes of HEV, the risk of cross-reactivity between the different oligonucleotides is minimized. Additional oligonucleotides may be used for the internal control. As it is not necessary to separately identify the different genotypes of HEV, the methods, set of primers, oligonucleotides and kit of the present invention are also cost effective since only a single test can be run to determine if any of the four genotypes of HEV is present in a sample.

The above specific embodiments of primer combinations can be further combined with one probe with a nucleic acid sequence selected from the group consisting of SEQ ID NO: 15 to 19 and 21. In one specific embodiment, the probe nucleic acid sequence is selected from the group consisting of SEQ ID NO: 15 to 18. In a more specific embodiment, the probe nucleic acid sequence is selected from SEQ ID NO: 15 or 18. In one specific embodiment, the probe nucleic acid sequence consists of SEQ ID NO: 15. In one specific embodiment, the probe nucleic acid sequence consists of SEQ ID NO: 18.

Tables 1 A to C show that with the present method, primers, probes, use and kit a better hit rate is obtained in the 5'UTR compared to using non-degenerate primers and probes in the Capsid (ORF2) region when using 500 cp/ml target and detecting GT3 or GT1, GT3 and GT4. (GT means genotype). A representative sequence for HEV GT1 5'UTR is SEQ ID NO: 38, for HEV GT2 5'UTR is SEQ ID NO: 39, for HEV GT3 5'UTR is SEQ ID NO: 40, for HEV GT4 5'UTR is SEQ ID NO: 41. A representative sequence for HEV GT1 CAPSID is SEQ ID NO: 42, for HEV GT2 CAPSID is SEQ ID NO: 43, for HEV GT3 CAPSID is SEQ ID NO: 44, for HEV GT4 CAPSID is SEQ ID NO: 45.

In one aspect, the probe comprises a fluorophore and a quencher. In one specific aspect, the probe comprises a fluorophore coupled to the 5' end of the probe and a quencher, wherein the spacing between fluorophore and quencher comprises at least 9 nucleotides. The term "spacing" relates to the number of nucleotides between fluorophore and quencher. In other specific aspects, the probe comprises at least 10 or at least 11 or at least 12 nucleotides between fluorophore and quencher. In one specific embodiment, the probe comprises 12 nucleotides between fluorophore and quencher.

Detection using a fluorophore and a quencher coupled to the probe is a well known detection method for real-time amplification of nucleic acids. Energy transfer between fluorophore and quencher in the unbound state of the probe leads to an abolishment of emission of fluorescent light by the excited fluorophore. In the hybridized state, the fluorophore and quencher are separated and the energy transfer is inhibited, resulting in light emission from the excited fluorophore. Fluorophores are dyes which emit fluorescent light of a certain wavelength following excitation. These dyes are used for detection. Examples of fluorophores include FAM, HEX, JA270, Cy5, Cy5.5, Coumarin etc. Fluorophores may be coupled to the 5' nucleic acid via a linker molecule. Such linker molecules are well known in the art. Non-limiting examples are threo-HEX, threo-FAM, threo-JA270 etc. Quenchers may belong to the group of Dark Quenchers. Non-limiting examples of such quenchers are Dabcyl, Eclipse, BHQ1, BHQ2, BBQ650, TAMRA. In one specific embodiment, the fluorophore is FAM or threo-FAM and the quencher is BHQ2.

Tables 4 and 6 show that by increasing the spacing between fluorophore and quencher a better hit rate for GT4 detection with a non-degenerate probe sequence is obtained. Thus, in one specific aspect, the probe comprises a nucleic acid sequence which consists of a nucleic acid sequence selected from the group consisting of SEQ ID NOS: 15-18 and SEQ ID NO:25.

In one specific embodiment, the probe comprises a T in position 86. Tables 4 to 6 show that a C in this position of the probe interferes with detection of all three genotypes. Thus, in one specific aspect, the probe comprises a nucleic acid sequence which consists of a nucleic acid sequence selected from the group consisting of SEQ ID NOS: 15-18 and SEQ ID NO:25.

In one specific aspect, the nucleotide in position 75 is an A. Tables 4, 6 and 7 show that probes with an A in this position lead to a better hit rate than probes with a G in this position. Thus, in one specific embodiment, the probe comprises a nucleic acid sequence which consists of SEQ ID NO:15 or SEQ ID NO:18.

In one aspect of the above methods, the methods additionally comprise, in parallel, the detection of a second target nucleic acid in a sample suspected to contain the second target nucleic acid, wherein the second nucleic acid is amplified and detected in vessels in which HEV is not amplified and detected, HEV is amplified and detected in vessels in which the second target nucleic acid is not amplified and detected, and wherein the vessels in which HEV is amplified and detected and the vessels in which the second target nucleic acid is amplified and detected are held in the same thermal block and cycled under identical conditions. This allows optimizing the throughput of a nucleic acid testing system since different tests can be run simultaneously in the same batch process. Amplification and detection of a second target nucleic acid can also be performed in the same vessel in which HEV is amplified and detected. For example simultaneous amplification and detection of a second or third or more viruses in addition to HEV can be performed in the same vessel by providing additional oligonucleotides specific for the second or third or more viruses.

In one aspect, the invention relates to a set of primers comprising a forward and at least one reverse primer, or at least one forward and one reverse primer, wherein the nucleic acid sequence of the forward primer or at least one forward primer is selected from the group consisting of SEQ ID NOS: 1-6, and wherein the nucleic acid sequence of the reverse primer or the at least one reverse primer is selected from the group consisting of SEQ ID NOS: 7-14. Specific embodiments of the primers and their advantages are as disclosed herein.

In one aspect the invention relates to a set of oligonucleotides, wherein the set consists of a set of primers as described herein and one probe, wherein the probe comprises at least 20 contiguous nucleotides of the nucleic acid sequence SEQ ID NOS: 15-19 or a complementary sequence thereof. Specific embodiments of the primers and probes and their advantages are as disclosed herein.

In one aspect, the invention relates to the use of a set of primers or a set of oligonucleotides as described herein for simultaneously detecting genotypes 1, 2, 3 and/or 4 of HEV in a biological sample. Specific embodiments of the use set of primers or set of oligonucleotides are as disclosed herein.

In one aspect, the invention relates to a kit comprising a template dependent DNA polymerase, nucleotides and a set of primers or a set of oligonucleotides as described herein. Specific embodiments of the primers or oligonucleotides are as described herein. Further the kit may comprise for example buffers, controls, internal control, external control, dyes, additional polymerases, and possible other amplification components well known in the art. Further the kit may provide instructions and analysis software.

Also disclosed is a method for determining if a sample comprises one or more of genotypes 1, 2, 3 and/or 4 of HEV comprising the steps of amplifying genotypes 1, 2, 3 and/or 4 of HEV according to the method described herein. A method is also disclosed for determining if a sample comprises one or more of genotypes 1, 2, 3 and/or 4 of HEV comprising the steps of simultaneously detecting genotypes 1, 2, 3 and/or 4 of HEV, if present in a sample, as described herein.

EXAMPLES

It is understood that the examples and embodiments described herein are for illustrative purposes only and are not intended to limit the scope of the claimed invention.

Sample Preparation

Armored RNA was prepared for HEV GT1, GT2, GT3 and GT4 by methods known in the art and used as a template.

50 cp/ml or 500 cp/ml of the HEV genotypes were prepared in advance and stored overnight (plasma dilutions at −60 to −90° C.):

Each respective sample (850 ul) was pipetted into a deep well plate for triplicate analysis. To each well containing a sample, 50 ul of an internal control nucleic acid were added. A control RNA (IC/QS) serving as a qualitative control was added (300 armored particles/sample).

The sequence of the control nucleic acids was identical in all cases and selected from the group of SEQ ID NOS: 46-49.

The respective control nucleic acid was stored in the following buffer:

| IC/QS - Storage Buffer | Conc. or pH |
|---|---|
| Tris (mM) | 10 |
| EDTA (mM) | 0.1 |
| Sodium Azide (w/v, %) | 0.05 |
| Poly rA RNA (mg/l) | 20 |
| pH | 8 |

Sample preparation was performed automatically, following the workflow according to the scheme depicted in FIG. 1 and using the following reagents:

| Protease reagent | Conc. or pH |
|---|---|
| Tris (mM) | 10 |
| EDTA (mM) | 1 |
| Calcium Chloride (mM) | 5 |
| Calcium Acetate (mM) | 5 |
| Esperase (mg/ml) | 80 |
| Glycerin (w/v, %) | 50 |
| pH | 5.5 |

| MGP Reagent | Conc. or pH |
|---|---|
| MPG Powder (mg/ml) | 60 |
| Tris (mM) | 30 |
| Methylparaben (w/v, %) | 0.1 |
| Sodium Azide (w/v, %) | 0.095 |
| pH | 8.5 |

| Lysis Reagent | Conc. or pH |
|---|---|
| Guanidine Thiocyanate (M) | 4 |
| Sodium Citrate (mM) | 50 |
| Polydocanol (w/v, %) | 5 |
| Dithiotreitol (w/v, %) | 2 |
| pH | 5.8 |

| Wash buffer | Conc. or pH |
|---|---|
| Sodium Citrate (mM) | 7.5 |
| Methylparaben (w/v, %) | 0.1 |
| pH | 4.1 |

| Elution buffer | Conc. or pH |
|---|---|
| Tris (mM) | 30 |
| Methylparaben (w/v, %) | 0.2 |
| pH | 8.5 |

After the final step, the respective master mixes (MMxs) containing amplification reagents were added to each well, the eluates containing the isolated nucleic acids were mixed with the MMx and each resulting mixture was transferred to a corresponding well of a microwell plate in which the amplification was carried out.

Amplification and Detection

For amplification, two solutions R1 and R2 of the following concentrations in a total volume of 50 ul were used:

R1: 16.73 mM MnOAc, pH 6.1, and 0.09% Sodium azide pH 7.0.

R2: 0.09% Sodium azide pH 7.0, 18% DMSO, 400 mM KOAc pH 7.0, 10% Glycerol, 0.05% Tween 20, 200 mM Tricine pH 8.0, 0.7 uM aptamer, 10 U UNG, 1.333 mM dGTP, 1.333 mM dATP, 1.333 mM dCTP, 2.667 mM dUTP, 45 U Z05D polymerase (per reaction), 0.667 uM HEV fwd primer, 0.417 uM HEV sense probe, 0.333 uM HEV rev primer; 0.417 uM control forward primer (SEQ ID NO:50), 0.417 uM control reverse primer (SEQ ID NO:51), 0.333 uM control probe (SEQ ID NO:52).

When two reverse primers were used, each was used at a concentration of 0.333 uM.

The following PCR profile was used:

Thermocycling Profile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
|  | 94 | None | 00:00:05 | 4.4 |  |  |
|  | 55 | None | 00:02:00 | 2.2 |  |  |
|  | 60 | None | 00:06:00 | 4.4 |  |  |
|  | 65 | None | 00:04:00 | 4.4 |  |  |
| 1st Measurement | 95 | None | 00:00:05 | 4.4 | 5 | Quantification |
|  | 55 | Single | 00:00:30 | 2.2 |  |  |
| 2nd Measurement | 91 | None | 00:00:05 | 4.4 | 45 | Quantification |
|  | 58 | Single | 00:00:25 | 2.2 |  |  |
| Cooling | 40 | None | 00:02:00 | 2.2 | 1 | None |

The Pre-PCR program comprises initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription.

PCR cycling is divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Amplification of HEV genotypes 1, 2, 3 and 4 was tested with different combinations of primers and probes and the hit rate determined, using either 500 cp/ml HEV or 50 cp/ml HEV. The results are shown in the following tables.

5'UTR primers and probes provide consistently better hit rates at 500 cp/ml HEV than Capsid primers and probes for detection of all genotypes, especially for GT3 and GT4 detection (Tables 1A to 1 C).

TABLE 1A

| Capsid, 500 cp/ml, GT3 | | | | |
|---|---|---|---|---|
| Forward | Reverse | Probe | hits | hit rate |
| SEQ ID NO: 26 | SEQ ID NO: 27 | SEQ ID NO: 32 | 0/10 (GT3) | 0 |
| SEQ ID NO: 26 | SEQ ID NO: 28 | SEQ ID NO: 32 | 0/10 (GT3) | 0 |
| SEQ ID NO: 26 | SEQ ID NO: 29 | SEQ ID NO: 32 | 1/10 (GT3) | 10 |
| SEQ ID NO: 26 | SEQ ID NO: 30 | SEQ ID NO: 32 | 4/10 (GT3) | 40 |
| SEQ ID NO: 26 | SEQ ID NO: 31 | SEQ ID NO: 32 | 0/10 (GT3) | 0 |

TABLE 1B

| 500 cp/ml: CAPSID, different GTs | | | | |
|---|---|---|---|---|
| Forward | Reverse | Probe | hits | hit rate |
| SEQ ID NO: 26 | SEQ ID NO: 30 | SEQ ID NO: 33 | 8/10 (GT3) | 80 |
|  |  |  | 10/10 (GT1) | 100 |
|  |  |  | 7/10 (GT4) | 70 |
| SEQ ID NO: 26 | SEQ ID NO: 30 | SEQ ID NO: 34 | 6/10 (GT3) | 60 |
|  |  |  | 8/10 (GT1) | 80 |
|  |  |  | 7/10 (GT4) | 70 |
| SEQ ID NO: 26 | SEQ ID NO: 30 | SEQ ID NO: 35 | 9/10 (GT3) | 90 |
|  |  |  | 10/10 (GT1) | 100 |
|  |  |  | 7/10 (GT4) | 70 |

TABLE 1C

| | | | 500 cp/ml: UTR, different GTs | | |
|---|---|---|---|---|---|
| SEQ ID NO: 6 | SEQ ID NO: 13 SEQ ID NO: 14 | SEQ ID NO: 15 | 10/10 | (GT1) | 100 |
| | | | 10/10 | (GT3) | 100 |
| | | | 10/10 | (GT4) | 100 |
| SEQ ID NO: 6 | SEQ ID NO: 13 SEQ ID NO: 14 | SEQ ID NO: 19 | 10/10 | (GT1) | 100 |
| | | | 10/10 | (GT3) | 100 |
| | | | 10/10 | (GT4) | 100 |
| SEQ ID NO: 6 | SEQ ID NO: 13 SEQ ID NO: 14 | SEQ ID NO: 22 | 10/10 | (GT1) | 100 |
| | | | 10/10 | (GT3) | 100 |
| | | | 10/10 | (GT4) | 100 |

Table 1D shows that with a Capsid primer/probe combination giving a 90% hit rate with 500 cp/ml HEV, the hit rate is significantly lower when decreasing the target nucleic acid to 50 cp/ml. With a primer/probe combination from the 5'UTR region, the hit rate remains high even when decreasing the target to 50 cp/ml.

TABLE 1 D

| | | | 50 cp/ml vs 500 cp/ml | | | |
|---|---|---|---|---|---|---|
| GT | | Fwd primer | Rev primer | probe | Hit rate | Hit rate % |
| | | | Capsid | | | |
| | 50 cp/mL | SEQ ID NO: 36 | SEQ ID NO: 30 | SEQ ID NO: 32 + SEQ ID NO: 37 | 7/20 (GT3) | 35 |
| | 500 cp/mL | | | | 9/10 (GT3) | 90 |
| | | | UTR | | | |
| 1 | 500 cp/mL | SEQ ID NO: 6 | SEQ ID NO: 13 SEQ ID NO: 14 | SEQ ID NO: 16 | 10/10 | 100 |
| 3 | | | | | 10/10 | 100 |
| 4 | | | | | 10/10 | 100 |
| 1 | 50 cp/mL | | | | 21/21 | 100 |
| 3 | | | | | 18/21 | 85.7 |
| 4 | | | | | 11/21 | 52.4 |

Table 2 shows the hit rates of different forward and reverse primer combinations for GT3 detection of HEV using 500 cp/ml HEV. Several forward and reverse primer pairs gave a 100% hit rate, while other combinations still provided good hit rates, as can be seen in Table 2.

TABLE 2

| Fwd primer | Rev primer | probe | Hit rate | Hit rate % |
|---|---|---|---|---|
| SEQ ID NO: 1 | SEQ ID NO: 12 | SEQ ID NO: 15 | 1/11 | 9 |
| SEQ ID NO: 20 | SEQ ID NO: 12 | SEQ ID NO: 15 | 0/11 | 0 |
| SEQ ID NO: 2 | SEQ ID NO: 12 | SEQ ID NO: 15 | 0/11 | 0 |
| SEQ ID NO: 3 | SEQ ID NO: 12 | SEQ ID NO: 15 | 9/11 | 82 |
| SEQ ID NO: 4 | SEQ ID NO: 12 | SEQ ID NO: 15 | 11/11 | 100 |
| SEQ ID NO: 5 | SEQ ID NO: 12 | SEQ ID NO: 15 | 0/11 | 0 |
| SEQ ID NO: 1 | SEQ ID NO: 7 | SEQ ID NO: 15 | 0/11 | 0 |
| SEQ ID NO: 20 | SEQ ID NO: 7 | SEQ ID NO: 15 | 0/11 | 0 |
| SEQ ID NO: 2 | SEQ ID NO: 7 | SEQ ID NO: 15 | 2/11 | 18 |
| SEQ ID NO: 3 | SEQ ID NO: 7 | SEQ ID NO: 15 | 8/11 | 73 |
| SEQ ID NO: 4 | SEQ ID NO: 7 | SEQ ID NO: 15 | 11/11 | 100 |
| SEQ ID NO: 5 | SEQ ID NO: 7 | SEQ ID NO: 15 | 0/11 | 0 |
| SEQ ID NO: 1 | SEQ ID NO: 8 | SEQ ID NO: 15 | 9/11 | 82 |
| SEQ ID NO: 20 | SEQ ID NO: 8 | SEQ ID NO: 15 | 3/11 | 27 |
| SEQ ID NO: 2 | SEQ ID NO: 8 | SEQ ID NO: 15 | 9/11 | 82 |
| SEQ ID NO: 3 | SEQ ID NO: 8 | SEQ ID NO: 15 | 11/11 | 100 |
| SEQ ID NO: 4 | SEQ ID NO: 8 | SEQ ID NO: 15 | 11/11 | 100 |
| SEQ ID NO: 5 | SEQ ID NO: 8 | SEQ ID NO: 15 | 3/11 | 27 |
| SEQ ID NO: 1 | SEQ ID NO: 9 | SEQ ID NO: 15 | 11/11 | 11 |
| SEQ ID NO: 20 | SEQ ID NO: 9 | SEQ ID NO: 15 | 4/11 | 36 |
| SEQ ID NO: 2 | SEQ ID NO: 9 | SEQ ID NO: 15 | 10/11 | 91 |
| SEQ ID NO: 3 | SEQ ID NO: 9 | SEQ ID NO: 15 | 11/11 | 100 |
| SEQ ID NO: 4 | SEQ ID NO: 9 | SEQ ID NO: 15 | 11/11 | 100 |
| SEQ ID NO: 5 | SEQ ID NO: 9 | SEQ ID NO: 15 | 7/11 | 64 |
| SEQ ID NO: 1 | SEQ ID NO: 10 | SEQ ID NO: 15 | 11/11 | 100 |
| SEQ ID NO: 20 | SEQ ID NO: 10 | SEQ ID NO: 15 | 0/11 | 0 |
| SEQ ID NO: 2 | SEQ ID NO: 10 | SEQ ID NO: 15 | 11/11 | 100 |
| SEQ ID NO: 3 | SEQ ID NO: 10 | SEQ ID NO: 15 | 11/11 | 100 |
| SEQ ID NO: 4 | SEQ ID NO: 10 | SEQ ID NO: 15 | 11/11 | 100 |
| SEQ ID NO: 5 | SEQ ID NO: 10 | SEQ ID NO: 15 | 9/11 | 82 |
| SEQ ID NO: 6 | SEQ ID NO: 13 | SEQ ID NO: 15 | 11/11 | 100 |

Table 3 shows the results of amplifications using different forward and reverse primer combinations from the 5'UTR region resulting in high hit rates of 77 to 100% for GT3 detection for several combinations even if only 50 cp/ml of HEV were used.

TABLE 3

| | 50 cp/mL, GT3 | | | |
|---|---|---|---|---|
| Fwd primer | Rev primer | probe | Hit rate | Hit rate % |
| SEQ ID NO: 4 | SEQ ID NO: 7 | SEQ ID NO: 15 | 0/22 | 0 |
| SEQ ID NO: 24 | SEQ ID NO: 7 | SEQ ID NO: 15 | 6/22 | 27 |
| SEQ ID NO: 6 | SEQ ID NO: 7 | SEQ ID NO: 15 | 17/22 | 77 |
| SEQ ID NO: 23 | SEQ ID NO: 7 | SEQ ID NO: 15 | 0/22 | 0 |
| SEQ ID NO: 4 | SEQ ID NO: 11 | SEQ ID NO: 15 | 2/22 | 9 |
| SEQ ID NO: 24 | SEQ ID NO: 11 | SEQ ID NO: 15 | 11/22 | 50 |
| SEQ ID NO: 6 | SEQ ID NO: 11 | SEQ ID NO: 15 | 19/22 | 86 |
| SEQ ID NO: 23 | SEQ ID NO: 11 | SEQ ID NO: 15 | 1/22 | 5 |
| SEQ ID NO: 4 | SEQ ID NO: 13 | SEQ ID NO: 15 | 0/22 | 0 |
| SEQ ID NO: 24 | SEQ ID NO: 13 | SEQ ID NO: 15 | 0/22 | 0 |
| SEQ ID NO: 6 | SEQ ID NO: 13 | SEQ ID NO: 15 | 22/22 | 100 |
| SEQ ID NO: 23 | SEQ ID NO: 13 | SEQ ID NO: 15 | 0/22 | 0 |
| SEQ ID NO: 4 | SEQ ID NO: 14 | SEQ ID NO: 15 | 0/22 | 0 |

TABLE 3-continued 50 cp/mL, GT3

| Fwd primer | Rev primer | probe | Hit rate | Hit rate % |
|---|---|---|---|---|
| SEQ ID NO: 24 | SEQ ID NO: 14 | SEQ ID NO: 15 | 0/22 | 0 |
| SEQ ID NO: 6 | SEQ ID NO: 14 | SEQ ID NO: 15 | 2/22 | 9 |
| SEQ ID NO: 23 | SEQ ID NO: 14 | SEQ ID NO: 15 | 0/22 | 0 |

Table 4 shows the results of tests using different probes combined with a specific forward primer and a mixture of two reverse primers. One probe did not perform. All of the other probes gave high hit rates for GT1 detection and somewhat lower hit rates for GT3 detection when using only 50 cp/ml. Differences were seen with GT4 detection at 50 cp/ml HEV, with several probe sequences giving reasonable hit rates for GT4 detection above 50%, and two probes giving good GT4 detection with hit rates above 70% combined with hit rates above 90% for GT3 detection and 100% for GT1 detection.

TABLE 4

Probes UTR

| GT | | Fwd primer | Rev primer | probe | Hit rate | Hit rate % |
|---|---|---|---|---|---|---|
| 1 | 500 cp/mL | SEQ ID NO: 6 | SEQ ID NO: 13 | SEQ ID NO: 19 | 10/10 | 100 |
| 3 | | | SEQ ID NO: 14 | | 10/10 | 100 |
| 4 | | | | | 10/10 | 100 |
| 1 | 50 cp/mL | | | | 21/21 | 100 |
| 3 | | | | | 20/21 | 95.2 |
| 4 | | | | | 8/21 | 38.1 |
| 1 | 500 cp/mL | SEQ ID NO: 6 | SEQ ID NO: 13 | SEQ ID NO: 15 | 10/10 | 100 |
| 3 | | | SEQ ID NO: 14 | | 10/10 | 100 |
| 4 | | | | | 10/10 | 100 |
| 1 | 50 cp/mL | | | | 21/21 | 100 |
| 3 | | | | | 20/21 | 95.2 |
| 4 | | | | | 16/21 | 76.2 |
| 1 | 500 cp/mL | SEQ ID NO: 6 | SEQ ID NO: 13 | SEQ ID NO: 21 | 0/10 | 0 |
| 3 | | | SEQ ID NO: 14 | | 0/10 | 0 |
| 4 | | | | | 0/10 | 0 |
| 1 | 50 cp/mL | | | | 0/21 | 0 |
| 3 | | | | | 0/21 | 0 |
| 4 | | | | | 0/20 | 0 |
| 1 | 500 cp/mL | SEQ ID NO: 6 | SEQ ID NO: 13 | SEQ ID NO: 16 | 10/10 | 100 |
| 3 | | | SEQ ID NO: 14 | | 10/10 | 100 |
| 4 | | | | | 10/10 | 100 |
| 1 | 50 cp/mL | | | | 21/21 | 100 |
| 3 | | | | | 18/21 | 85.7 |
| 4 | | | | | 11/21 | 52.4 |
| 1 | 500 cp/mL | SEQ ID NO: 6 | SEQ ID NO: 13 | SEQ ID NO: 17 | 10/10 | 100 |
| 3 | | | SEQ ID NO: 14 | | 10/10 | 100 |
| 4 | | | | | 10/10 | 100 |
| 1 | 50 cp/mL | | | | 21/21 | 100 |
| 3 | | | | | 19/21 | 90.5 |
| 4 | | | | | 12/21 | 57.1 |
| 1 | 500 cp/mL | SEQ ID NO: 6 | SEQ ID NO: 13 | SEQ ID NO: 18 | 10/10 | 100 |
| 3 | | | SEQ ID NO: 14 | | 10/10 | 100 |
| 4 | | | | | 10/10 | 100 |
| 1 | 50 cp/mL | | | | 21/21 | 100 |
| 3 | | | | | 20/21 | 95.2 |
| 4 | | | | | 15/21 | 71.4 |

Table 5 shows that the primer and probe sequences detect all four HEV genotypes, GT1, GT2, GT3 and GT4.

TABLE 5

| GT | | Fwd primer | Rev primer | probe | Hit rate | Hit rate % |
|---|---|---|---|---|---|---|
| 2 | 150 cp/mL | SEQ ID NO: 6 | SEQ ID NO: 13 | SEQ ID NO: 18 | 38/40 | 95 |
| 4 | | | SEQ ID NO: 14 | | 35/40 | 87.5 |
| 1 | 30 cp/mL | | | | 42/42 | 100 |
| 2 | | | | | 37/42 | 88.1 |
| 3 | | | | | 42/42 | 100 |
| 4 | | | | | 42/42 | 100 |

Table 6 shows an alignment of different probe sequences. As can be seen, the sequences of the different probes are almost identical. The differences relate, on the one hand, to a different position of the Quencher Q within the probe. The other differences represent non-conserved nucleotides in the different genotypes. The differing positions are also shown in Table 7. A comparison of the sequence differences and the hit rates obtained, as shown in Table 4, shows that not all of these positions are of relevance for the performance of the probe sequences. A T in position 86 benefits the performance of the probe sequence. An A in position 75 also has a beneficial effect on probe performance for detection of GT4. Furthermore, a spacing of 9 or more nucleotides between fluorophore and Quencher improves performance of the HEV 5'UTR probes.

TABLE 6

```
                75        86
                ↓         ↓
FAAGGCTCCTGGCQATCACTACTGCTATTGAGCAGGC   SEQ ID NO: 15

FAAGGCTCCTGGCQGTCACTACTGCTATTGAGCAGGC   SEQ ID NO: 16

FAAGGCTCCTGGCQGTCACAACTGCTATTGAGCAGGC   SEQ ID NO: 17

FAAGGCTCCTGGCQATTACTACTGCTATTGAGCAGGC   SEQ ID NO: 18

FAAGGCTCCQTGGCATCACTACTGCTATTGAGCAGG    SEQ ID NO: 19
```

TABLE 6 -continued

```
FAAGGCTCCTGGCQATTACTACTGCCATTGAGCAGGC   SEQ ID NO: 21

FAAGGCTCCTGGCQATTACAACTGCTATTGAGCAGGC   SEQ ID NO: 25
```

TABLE 7

|  | Pos 75 | Pos 77 | Pos 80 | Pos 86 |
|---|---|---|---|---|
| SEQ ID NO: 15 | A | C | T | T |
| SEQ ID NO: 21 | A | T | T | C |
| SEQ ID NO: 16 | G | C | T | T |
| SEQ ID NO: 17 | G | C | A | T |
| SEQ ID NO: 18 | A | T | T | T |
| SEQ ID NO: 19 | A | C | T | T |

Table 8A shows the detection of all four genotypes, GT1, GT2, GT3 and GT4, using primer combinations SEQ ID NO: 6 with a mixture of SEQ ID NO: 13 and SEQ ID NO: 14, and SEQ ID NO: 6 with SEQ ID NO:11. As can be seen in the table, at 500 cp/ml of HEV, all four genotypes are efficiently amplified by the primer combinations as the hit rate is 100% for each genotype. At the lower concentration of 50 cp/ml HEV, the hitrates are still high and the four HEV genotypes are all amplified with a hit rate between 75 and 100%. In contrast, using other primer combinations from the same region of HEV, as shown in Table 8 B, only gt 2, gt3 and gt4 are efficiently amplified when using 500 cp/ml of HEV. At 50 cp/ml HEV, not all genotypes can be amplified. The hitrates of the corresponding internal controls were 100% for each experiment.

TABLE 8A

| GT |  | Fwd primer | Rev primer | probe | Hit rate | Hit rate % |
|---|---|---|---|---|---|---|
| 1 | 500 cp/mL | SEQ ID NO: 6 | SEQ ID NO: 13 | SEQ ID NO: 15 | 3/3 | 100 |
| 2 |  |  | SEQ ID NO: 14 |  | 3/3 | 100 |
| 3 |  |  |  |  | 3/3 | 100 |
| 4 |  |  |  |  | 3/3 | 100 |
| 1 | 50 cp/mL |  |  |  | 19/20 | 95 |
| 2 |  |  |  |  | 20/20 | 100 |
| 3 |  |  |  |  | 15/20 | 75 |
| 4 |  |  |  |  | 19/19 | 100 |
| 1 | 500 cp/mL | SEQ ID NO: 6 | SEQ ID NO: 11 | SEQ ID NO: 15 | 3/3 | 100 |
| 2 |  |  |  |  | 3/3 | 100 |
| 3 |  |  |  |  | 3/3 | 100 |
| 4 |  |  |  |  | 3/3 | 100 |
| 1 | 50 cp/mL |  |  |  | 19/20 | 95 |
| 2 |  |  |  |  | 20/20 | 100 |
| 3 |  |  |  |  | 17/20 | 85 |
| 4 |  |  |  |  | 20/20 | 100 |

Table 8 B shows detection patterns for different genotypes which yielded a signal at a high HEV titer for genotype 3 using primer combinations SEQ ID NO: 4 and 8, SEQ ID NO: 3 and 9. Detection of the HEV genotypes 1, 2, 3, 4 with 500 cp/ml and 50 cp/ml HEV is shown. Recognition of genotype 2 is generally better than recognition of genotypes 1 and 3. The hitrates of the corresponding internal controls were 100% for each experiment.

TABLE 8B

| GT |  | Fwd primer | Rev primer | probe | Hit rate | Hit rate % |
|---|---|---|---|---|---|---|
| 1 | 500 cp/ml | SEQ ID NO: 4 | SEQ ID NO: 8 | SEQ ID NO: 15 | 0/3 | 0 |
| 2 |  |  |  |  | 3/3 | 100 |
| 3 |  |  |  |  | 3/3 | 100 |
| 4 |  |  |  |  | 3/3 | 100 |
| 1 | 50 cp/ml | SEQ ID NO: 4 | SEQ ID NO: 8 | SEQ ID NO: 15 | 0/20 | 0 |
| 2 |  |  |  |  | 14/20 | 70 |

TABLE 8B-continued

| GT | | Fwd primer | Rev primer | probe | Hit rate | Hit rate % |
|---|---|---|---|---|---|---|
| 3 | | | | | 0/20 | 0 |
| 4 | | | | | 6/20 | 32 |
| 1 | 500 cp/ml | SEQ ID NO: 3 | SEQ ID NO: 9 | SEQ ID NO: 15 | 0/3 | 0 |
| 2 | | | | | 3/3 | 100 |
| 3 | | | | | 2/3 | 67 |
| 4 | | | | | 3/3 | 100 |
| 1 | 50 cp/ml | SEQ ID NO: 3 | SEQ ID NO: 9 | SEQ ID NO: 15 | 0/19 | 0 |
| 2 | | | | | 15/20 | 75 |
| 3 | | | | | 0/20 | 0 |
| 4 | | | | | 0/20 | 32 |

Table 9 shows the results of a cross reactivity testing for the primer and probe combinations SEQ ID NOS: 6, 13, 14, 15 (Table 9 A) and SEQ ID NOS: 6, 11, 15 (Table 9 B).

Cross reactivity was tested under the conditions described above. The following concentrations of microorganisms were used: Streptococcus viridians (oralis): 1.00 E+06 cfu/ml; HAV: 1.00E+06 cp/ml; HBV: 1.00E+06 IU/ml; HCV: 1.00E+06 IU/ml; NSC: negative spike control: no addition of microorganism; PSC: positive spike control: addition of 150 cp/ml HEV.

IC means internal control.

TABLE 9A

| SEQ ID NOS: 6, 13, 14, 15 | | | | |
|---|---|---|---|---|
| | Without HEV, hitrates, hitrates % | | With HEV, hitrates, hitrates % | |
| | HEV primers and probes | IC | HEV primers and probes | IC |
| Streptococcus viridian (oralis) | 0/3, 0% | 3/3, 100% | 3/3, 100% | 3/3, 100% |
| HAV | 0/3, 0% | 3/3, 100% | 3/3, 100% | 3/3, 100% |
| HIV-1M | 0/3, 0% | 3/3, 100% | 3/3, 100% | 3/3, 100% |
| HBV | 0/3, 0% | 3/3, 100% | 3/3, 100% | 3/3, 100% |
| HCV | 0/3, 0% | 3/3, 100% | 3/3, 100% | 3/3, 100% |
| NSC/PSC | 0/3, 0% | 3/3, 100% | 3/3, 100% | 3/3, 100% |

TABLE 9B

| SEQ ID NOS: 6, 11, 15 | | | | |
|---|---|---|---|---|
| | Without HEV, hitrates, hitrates % | | With HEV, hitrates, hitrates % | |
| | HEV primers and probes | IC | HEV primers and probes | IC |
| Streptococcus viridian (oralis) | 1/3, 33% | 3/3, 100% | 3/3, 100% | 3/3, 100% |
| HAV | 0/3, 0% | 3/3, 100% | 3/3, 100% | 3/3, 100% |
| HIV-1M | 0/3, 0% | 3/3, 100% | 3/3, 100% | 3/3, 100% |
| HBV | 1/3, 33% | 3/3, 100% | 3/3, 100% | 3/3, 100% |
| HCV | 0/3, 0% | 3/3, 100% | 3/3, 100% | 3/3, 100% |
| NSC/PSC | 0/3, 0% | 3/3, 100% | 3/3, 100% | 3/3, 100% |

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for simultaneously detecting the presence or absence of genotypes 1, 2, 3, and/or 4 of hepatitis E virus (HEV) in a biological sample, comprising the steps of:
   (a) isolating nucleic acids present in the biological sample;
   (b) amplifying the nucleic acids isolated in step (a) in a single reaction mixture, using one non-degenerate forward primer comprising SEQ ID NO: 6 and at least one non-degenerate reverse primer comprising a sequence selected from the group consisting of SEQ ID NOS: 11, 13, and 14, wherein the forward and reverse primers simultaneously amplify genotypes 1, 2, 3, and/or 4 of HEV, if present in the biological sample; and
   (c) detecting the presence or absence of amplified nucleic acid obtained in step (b), wherein the presence of amplified nucleic acid obtained in step (b) is an indication of the presence of genotypes 1, 2, 3, and/or 4 of HEV in the biological sample, and wherein the absence of amplified nucleic acid obtained in step (b) is an indication of the absence of genotypes 1, 2, 3, and/or 4 of HEV in the biological sample.

2. The method of claim 1, wherein the forward primer comprises SEQ ID NO: 6 and the at least one reverse primer comprises a sequence selected from the group consisting of SEQ ID NOS: 13 and 14.

3. The method of claim 1, wherein the amplifying step (b) uses at least two non-degenerate reverse primers comprising the sequences of SEQ ID NOS: 13 and 14, and wherein the forward primer comprises SEQ ID NO: 6.

4. The method of claim 1, wherein said isolating step (a) comprises binding the nucleic acids to a solid phase.

5. The method of claim 1, wherein the amplified nucleic acids are contacted with a nucleic acid probe under conditions sufficient for binding the probe to the amplified nucleic acids.

6. The method of claim 5, wherein the probe comprises at least 20 contiguous nucleotides of SEQ ID NOS: 15-19, or the complementary sequence thereof.

7. The method of claim 5, wherein the probe comprises at least 22 to 35 contiguous nucleotides of SEQ ID NOS: 15-19, or the complementary sequence thereof.

8. The method of claim 5, wherein the probe consists of a sequence selected from SEQ ID NOS: 15-19, or the complementary sequence thereof.

9. The method of claim 5, wherein the probe consists of a sequence selected from SEQ ID NO: 15-18.

10. The method of claim 5, wherein the probe comprises a fluorophore and a quencher.

11. The method of claim 10, wherein the fluorophore is coupled to the 5' end of the probe, and the spacing between the fluorophore and the quencher comprises at least 9 nucleotides.

12. The method of claim 1, wherein the forward primer comprises SEQ ID NO: 6 and the at least one reverse primer comprises SEQ ID NO: 11.

13. The method of claim 1, further comprising the step of:
   (c) detecting amplified nucleic acids obtained in step (b) as an indication of the presence of genotypes 1, 2, 3, and 4 of HEV in the biological sample.

14. The method of claim 13, wherein the amplified nucleic acids are contacted with a nucleic acid probe under conditions sufficient for binding the probe to the amplified nucleic acids.

15. The method of claim 14, wherein the probe comprises at least 20 contiguous nucleotides of SEQ ID NOS: 15 or 18, or the complementary sequence thereof.

16. The method of claim 14, wherein the probe comprises at least 22 to 35 contiguous nucleotides of SEQ ID NOS: 15 or 18, or the complementary sequence thereof.

17. The method of claim 14, wherein the probe consists of a sequence selected from SEQ ID NOS: 15 or 18, or the complementary sequence thereof.

18. The method of claim 14, wherein the probe consists of a sequence selected from SEQ ID NO: 15 or 18.

19. The method of claim 14, wherein the probe comprises a fluorophore and a quencher.

20. The method of claim 19, wherein the fluorophore is coupled to the 5' end of the probe, and the spacing between the fluorophore and the quencher comprises at least 9 nucleotides.

* * * * *

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtcgatgcca tggaggccca                                                    20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```

```
gtggtcgatg ccatggaggc cc                                              22
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gtggtcgatg ccatggaggc c                                               21
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gtggtcgatg ccatggaggc                                                 20
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
atgtggtcga tgccatggag gccca                                           25
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
atgccatgga ggcccatcag ttta                                            24
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
cgaaccacca cagcattcgc ca                                              22
```

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ggccgaacca ccacagcatt cgc                                             23
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gccgaaccac cacagcattc gc					22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccgaaccacc acagcattcg c					21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ggccgaacta ccacagcatt cgc					23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ggccgaacca ccacagcatt c					21

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
aaaggccgaa ccaccacagc attc					24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aaaggcctaa ctaccacagc attc					24

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
aaggctcctg gcatcactac tgctattgag caggc                              35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
aaggctcctg gcgtcactac tgctattgag caggc                              35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
aaggctcctg gcgtcacaac tgctattgag caggc                              35

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aaggctcctg gcattactac tgctattgag caggc                              35

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aaggctcctg gcatcactac tgctattgag cagg                               34

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtggtcgatg ccatggaggc cca                                           23

```
<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
aaggctcctg gcattactac tgccattgag caggc                                   35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaggctcctg gcattactac tgctattgag caggc                                   35

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgccatgga ggcccaccag ttca                                               24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgccatgga ggcccatcag ttca                                               24

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
aaggctcctg gcattacaac tgctattgag caggc                                   35

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcagtggttt ctggggtga                                                     19

<210> SEQ ID NO 27
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggttggttg gatgaatata                                                     20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcgaaggggt tggttggatg aa                                                  22

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgaaggggt tggttggatg aatata                                              26

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaggggttgg ttgatgaat ata                                                  23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaggggttgg ttgatgaat a                                                    21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgattctcag cccttcgccc tccc                                                24

<210> SEQ ID NO 33
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgattctcag cccttcgcaa tccc                                            24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgattctcag cccttcgccc tccc                                            24

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aagggctgag aatcaaccct gtcaccccca                                      29

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcagtggttt ctggggtgac                                                 20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgattctcag cccttcgcaa tccc                                            24

<210> SEQ ID NO 38
<211> LENGTH: 136
<212> TYPE: DNA
<213> ORGANISM: Hepatitis E virus
<220> FEATURE:
<221> NAME/KEY: misc_feature
<222> LOCATION: (1)..(136)
<223> OTHER INFORMATION: HEV_GT1_5'UTR_region

<400> SEQUENCE: 38
gcagaccaca tatgtggtcg atgccatgga ggcccatcag tttattaagg ctcatggcat     60
cactactgct attgagcagg ctgctctagc ggcggccaac tctgccctgg cgaatgctgt    120
ggtagttagg ccttttt                                                   136
```

<210> SEQ ID NO 39
<211> LENGTH: 136
<212> TYPE: DNA
<213> ORGANISM: Hepatitis E virus
<220> FEATURE:
<221> NAME/KEY: misc_feature
<222> LOCATION: (1)..(136)
<223> OTHER INFORMATION: HEV_GT2_5'UTR_region

<400> SEQUENCE: 39
gcagaccacg tatgtggtcg atgccatgga ggcccatcag ttcattaagg ctcctggcat    60
tactactgct attgagcagg ctgctctggc tgcggctaat ccgccttgg cgaatgctgt   120 ggtggttcgg ccgttt                                                  136

<210> SEQ ID NO 40
<211> LENGTH: 136
<212> TYPE: DNA
<213> ORGANISM: Hepatitis E virus
<220> FEATURE:
<221> NAME/KEY: misc_feature
<222> LOCATION: (1)..(136)
<223> OTHER INFORMATION: HEV_GT3_5'UTR_region

<400> SEQUENCE: 40
gcagaccacg catgtggtcg atgccatgga ggcccatcag tttattaagg ctcctggcat    60
tactactgcc attgagcagg ctgctctggc tgcggccaac tccgccttgg cgaatgctgt   120
ggtggttcgg ccgttt                                                  136

<210> SEQ ID NO 41
<211> LENGTH: 136
<212> TYPE: DNA
<213> ORGANISM: Hepatitis E virus
<220> FEATURE:
<221> NAME/KEY: misc_feature
<222> LOCATION: (1)..(136)
<223> OTHER INFORMATION: HEV_GT4_5'UTR_region

<400> SEQUENCE: 41
gcagaccacg tatgtggtcg acgccatgga ggcccaccag ttcataaagg ctcctggcgt    60
cactactgct attgagcagg cagctctagc agcggccaac tccgccttgg cgaatgctgt   120
ggtggttcgg cctttc                                                  136

<210> SEQ ID NO 42
<211> LENGTH: 150
<212> TYPE: DNA
<213> ORGANISM: Hepatitis E virus
<220> FEATURE:
<221> NAME/KEY: misc_feature
<222> LOCATION: (1)..(150)
<223> OTHER INFORMATION: HEV_GT1_CAPSID_region

<400> SEQUENCE: 42
ttgcctatgt tgcccgcgcc accgcccggt cagccgtctg gccgccgtcg tgggcggcgc    60
agcggcggtt ccggcggtgg tttctggggt gaccggggttg attctcagcc cttcgcaatc   120
ccctatattc atccaaccaa ccccttcgcc                                   150

<210> SEQ ID NO 43
<211> LENGTH: 150
<212> TYPE: DNA
<213> ORGANISM: Hepatitis E virus
<220> FEATURE:

```
<221> NAME/KEY: misc_feature
<222> LOCATION: (1)..(150)
<223> OTHER INFORMATION: HEV_GT2_CAPSID_region

<400> SEQUENCE: 43
ttgcctatgc tgcccgcgcc accggccggc cagccgtctg gccgccgtcg tgggcggcgc      60
agcggcggtg ccggcggtgg tttctggggt gacagggttg attctcagcc cttcgccctc     120
ccctatattc atccaaccaa ccccttcgcc                                      150

<210> SEQ ID NO 44
<211> LENGTH: 150
<212> TYPE: DNA
<213> ORGANISM: Hepatitis E virus
<220> FEATURE:
<221> NAME/KEY: misc_feature
<222> LOCATION: (1)..(150)
<223> OTHER INFORMATION: HEV_GT3_CAPSID_region

<400> SEQUENCE: 44
ctgcctatgc tgcccgcgcc accggccggc cagccgtctg gccgccgtcg tgggcggcgc      60
agcggcggtg cgggcggtgg tttctggggt gacagggttg attctcagcc cttcgccctc     120
ccctatattc atccaaccaa ccccctttgcc                                     150

<210> SEQ ID NO 45
<211> LENGTH: 150
<212> TYPE: DNA
<213> ORGANISM: Hepatitis E virus
<220> FEATURE:
<221> NAME/KEY: misc_feature
<222> LOCATION: (1)..(150)
<223> OTHER INFORMATION: HEV_GT4_CAPSID_region

<400> SEQUENCE: 45
ctgcctatgc tgcccgcgcc accggccggt cagccgtctg gccgtcgccg cgggcggcgc      60
agcggcggtg ccggcggtgg tttctggggt gaccgggttg attctcagcc cttcgccctc     120
ccctatattc atccaaccaa ccccttcgca                                      150

<210> SEQ ID NO 46
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
aattcaagct tagatctagc tttgcctgct tgatagcaat cggctatcga ctaatgactg      60
tcctggcggt ctctcgccat ctcctaccgc attggctcat aggtaagctc gctgtcaccc     120
agtacggagg tgccagtaga ttattagaga cagtcgccaa tcgatcgtta taccgagatg     180
actgagtatc gaagctacat tgtagccgca cataggacca cccatcttca tgttgaaaca     240
tgaggattac ccatgtggat ccaagcttg                                       269

<210> SEQ ID NO 47
<211> LENGTH: 235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
```

```
gggctgcagg tcgactctag attctaagaa tttgatgggc ttttctact aattactatt    60 agtatattgc catctttaac acttagaccg aagtgtgctg aagttccagt ggccggccca   120
gacctgggaa gttgcaagga cttaaacgaa tgcaagcgat catatcttga aaaattataa   180
ccagaggatc gatgaaaaaa atttcttaga gctttggatc cccgggcgag ctccc        235
```

<210> SEQ ID NO 48
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
cgactctaga tgaagggagc cttagaacgg ggctgcgcta gctggcatca aagtccgtca    60
gagctcaacc ctccaacgag gattcctgaa tactcgaaag tcagtgtgca gttactaaca   120
acagctgctc gacctcgggg tctcgaacaa tccatacctg ctatcgctgc cttcagacat   180
acggatgggc taggaggcaa gagctacctg tctcaacgaa ctatcggagt gggacccgat   240
gaagctgtca gcgccacttc cggcggtaag gctttaaaac gcgcccgccg gttatcacgc   300
gcggggagca cagcgcggac tgacgtgctg ggaagcaccg gttaaggatc              350
```

<210> SEQ ID NO 49
<211> LENGTH: 470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
cgactctaga aactgggtag taactgcggg ggcgaatgat gcaggcttca gaaattaaac    60
tcaatagtat ccggtgtctc aatcttttc gggccaggcg gcggtggacg acagacaatt    120
ttacgatttt ggttccggtc acaaccgcgc catacatgtc aagaatgaag tgggcgaacg   180
ctagaaaact gacgccagca attaagtgag tcggggcgtg gtgactccca cgtaaaaagc   240
ccctaccccg caccgttacg aagtatcaaa acgggacgcg cacgaaccga cgattggtac   300
tgtataagcg gcccgacgaa ctcaaaatcc caagtgaatc tatgaaatct acatcgcgtt   360
tataatctac ggggtgtaaa cggatgagaa ttggccaaac ggaggcacac acgcgtgcaa   420
tgcgccgacc ctgagaaaag tatcatgtgc gtcggccaca ggatccccgg              470
```

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
ttgatagcaa tcggctatcg actaa                                          25
```

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic

```
    oligonucleotide

<400> SEQUENCE: 51
gcttcgatac tcagtcatct cggtataa                                              28

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tctctcgcca tctcctaccg cattggc                                               27
```